(12) United States Patent
Reddy et al.

(10) Patent No.: US 6,890,736 B1
(45) Date of Patent: May 10, 2005

(54) METHODS FOR PRODUCING PROTEINS IN CULTURED CELLS

(75) Inventors: Pranhitha Reddy, Seattle, WA (US); Brian D. Rasmussen, Bellevue, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 10/663,853

(22) Filed: Sep. 16, 2003

Related U.S. Application Data

(60) Provisional application No. 60/412,428, filed on Sep. 20, 2002.

(51) Int. Cl.$^7$ .................................................. C12P 21/06
(52) U.S. Cl. ..................... 435/69.1; 435/358; 536/22.1; 536/26.3
(58) Field of Search .............................. 435/69.1, 358; 536/22.1, 26.3

(56) References Cited

U.S. PATENT DOCUMENTS

| 5,503,975 | A | 4/1996 | Smith et al. |
| 6,184,211 | B1 | 2/2001 | Szyf |
| 6,268,137 | B1 | 7/2001 | Szyf et al. |
| 2002/0114809 | A1 | 8/2002 | Rubinfeld et al. |

FOREIGN PATENT DOCUMENTS

| EP | 0 287 128 A1 | 10/1988 |
| WO | WO 99/12027 | 3/1999 |

OTHER PUBLICATIONS

Tanigawa et al. Journal of Fermentation and Bioengineering 75(4): 254–258 (1993).*
Lucas et al. Nucleic Acids Research 24(9): 1774–1779 (1996).*
Alexeeva I et al., "6–Azacytidine—compound with wide spectrum of antiviral activity," Nucleosides Nucleotides Nucleic Acids 2001; 20(4–7):1147–1152.
Alexeeva I et al., "$N_4$–amino–acid derivatives of 6–azacytidine: structure–activity relationship," Acta Biochim Pol 2000; 47(1):95–101.
Bolden A et al., "DNA methylation. Inhibition of de novo and maintenance methylation in vitro by RNA and synthetic polynucleotides," J Biol Chem 1984; 259(20):12437–12443.
Broday L et al., "5–Azacytidine induces transgene silencing by DNA methylation in Chinese hamster cells," Mol Cell Biol 1999; 19(4):3198–3204.
Christman JK et al., "Correlation between hypomethylation of DNA and expression of globin genes in friend erythroleukemia cells," Eur J Biochem 1977; 81:53–61.
Di Ianni M et al., "In vivo demethylation of a MoMuLV retroviral vector expressing the herpes simplex thymidine kinase suicide gene by 5' azacytidine," Stem Cells 2000; 18:415–421.

Frostesjo L et al., "Interference with DNA methyltransferase activity and genome methylation during F9 teratocarcinoma stem cell differentiation induced by polyamine depletion," J Biol Chem 1997; 272(7):4359–4366.
Heby O, "DNA methylation and polyamines in embryonic development and cancer," Int J Dev Biol 1995; 39:737–757.
Izbicka E et al., "5,6 dihydro–5'–azacytidine (DHAC) restores androgen responsiveness in androgen–insensitive prostate cancer cells," Anticancer Res 1999; 19:1285–1292.
Izbicka E et al., "5,6–dihydro–5'–azacytidine (DHAC) affects estrogen sensitivity in estrogen–refractory human breast carcinoma cell lines," Anticancer Res 1999; 19:1293–1298.
Jones PA, "Altering gene expression with 5–azacytidine," Cell 1985; 40:485–486.
Jones PA and Taylor SM, "Cellular differentiation, cytidine analogs and DNA methylation," Cell 1980; 20:85–93.
Kissil JL et al., "DAP–kinase loss of expression in various carcinoma and B–cell lymphoma cell lines: possible implications for role as tumor suppressor gene," Oncogene 1997; 15:403–407.
Konieczny SF and Emerson, CP Jr., "5–azacytidine induction of stable mesodermal stem cell lineages from 10T1/2 cells: evidence for regulatory genes controlling determination," Cell 1984; 38:791–800.
Kusaba H et al., "Association of 5' CpG demethylation and altered chromatin structure in the promoter region with transcriptional activation of the multidrug resistance 1 gene in human cancer cells," Eur J Biochem 1999; 262:924–932.
McIntosh LP et al., "Synthesis and characterization of poly[d(G–$z^5$C)]. B–Z transition and inhibition of DNA methylase," Biochemistry 1985; 24:4806–4814.
Motoji T et al., "The effect of 5–azacytidine and its analogues on blast cell renewal in acute myeloblastic leukemia," Blood 1985; 65(4):894–901.
Nakayama H et al., "Possible involvement of DNA methylation in 5–azacytidine–induced neuronal cell apoptosis," Histol Histopathol 1999; 14:143–150.
Otterson GA et al., "CDKN2 gene silencing in lung cancer by DNA hypermethylation and kinetics of p16$^{INK4}$ protein induction by 5–aza 2'deoxycytidine," Oncogene 1995; 11:1211–1216.

(Continued)

Primary Examiner—Karen Cochrane Carlson
Assistant Examiner—Anand U Desai
(74) Attorney, Agent, or Firm—Rosemary Sweeney (57) ABSTRACT

The invention provides a method for increasing production of a protein by cultured mammalian cells comprising adding a DNA demethylating agent, for example a cytidine analogue, to the mammalian cell culture. The cytidine analogue can be 5-aza-2'-deoxycytidine (also called decitabine) or 5-bromo-2'-deoxycytidine-5'-monophosphate, among many other possible cytidine analogues.

29 Claims, 1 Drawing Sheet

OTHER PUBLICATIONS

Qian X et al., "DNA methylation regulates p27$^{Kip1}$ expression in rodent pituitary cell lines," *Am J Pathol* 1998; 153(5):1475–1482

Singal R et al., "Cytosine methylation represses glutathione S–transferase P1 (GSTP1) gene expression in human prostate cancer cells," *Cancer Res* 2001; 61:4820–4826.

Soultanas P et al., "Modulation of human DNA methyltransferase activity and mRNA levels in the monoblast cell line U937 induced differentiate with dibutyryl cyclic AMP and phorbol ester," *J Mol Endocrinol* 1993; 11:191–200.

Stopper H et al., "Micronuclei induced by modulators of methylation: analogs of 5–azacytidine," *Carcinogenesis* 1995; 16(7):1647–1650.

Szyf M et al., "Induction of myogenic differentiation by an expression vector encoding the DNA methyltransferase cDNA sequence in the antisense orientation," *J Biol Chem* 1992; 267(18):12831–12836.

Takebayashi S–i et al., "5–aza–2'–deoxycytidine induces histone hyperacetylation of mouse centromeric heterochromatin by a mechanism independent of DNA demethylation," *Biochem Biophys Res Commun* 2001; 288:921–926.

Wilson VL and Jones PA, "Inhibition of DNA methylation by chemical carcinogens in vitro," *Cell* 1983; 32:239–246.

\* cited by examiner

Figure 1

METHODS FOR PRODUCING PROTEINS IN CULTURED CELLS

This application claims benefit of U.S. Provisional Application No. 60/412,428, filed Sep. 20, 2002.

FIELD OF THE INVENTION

The invention relates to methods and media for increasing production of a protein produced by cultured cells, particularly cultured mammalian cells.

BACKGROUND

Proteins are commercially useful in a large variety of applications, including diagnostic, pharmacological, therapeutic, nutritional, and research applications. Large scale production of proteins for commercial use can be both laborious and expensive. Moreover, facilities that produce proteins for pharmacological use can incur significant cost to obtain building and regulatory approval. Thus, even small increases in the efficiency with which a protein can be produced are commercially valuable because of the limited number of facilities available for production and the expense of production.

Cultured mammalian cells have been used for production of some proteins, particularly recombinant proteins intended for pharmacological use, and numerous adjustments of culture conditions have been shown to affect the quantity and quality of protein produced. The present invention provides a new culture process that is designed to improve production of a protein, particularly a recombinant protein, from cultured mammalian cells.

SUMMARY

The invention provides methods for increasing production of a protein by mammalian cells comprising culturing mammalian cells in the presence of a DNA demethylating agent, which may be a cytidine analogue. More specifically, the invention provides a method for increasing production of a protein by cultured CHO cells comprising adding a cytidine analogue to the medium in which the CHO cells are cultured, whereby the production of the protein is increased. The cytidine analogue may be present at a concentration from about 0.01 $\mu$M to about 100 $\mu$M or from about 0.1 $\mu$M to about 50 $\mu$M. Culture conditions may include a temperature from about 29° C. to 36° C. The cytidine analogue may be 5-aza-2'-deoxycytidine, which may further comprise one or more phosphate groups attached to its 3' and/or 5'carbon(s). The protein may be an antibody or a recombinant protein and may be secreted into the medium. The mRNA encoding the protein may be transcribed starting from a viral promoter. The medium may be serum free, and the volume of the culture may be at least about 100 liters. Alternatively, the cytidine analogue may be 5-bromo-2'-deoxycytidine, which may further comprise one or more phosphate groups attached to its 3' and/or 5' carbon(s).

In one aspect, the invention provides a method for producing a recombinant protein in cultured mammalian cells that have been genetically engineered to produce the recombinant protein comprising growing the mammalian cells in a medium comprising a DNA demethylating agent, wherein the recombinant protein is secreted into the medium, and harvesting the medium comprising the recombinant protein, wherein the presence of the DNA demethylating agent in the medium results in an increase in the titer of the recombinant protein in the medium. The DNA demethylating agent can be a cytidine analogue. The cytidine analogue may be present at a concentration from about 0.01 $\mu$M to about 100 $\mu$M. The cytidine analogue may be 5-aza-2'-deoxycytidine and/or 5-bromo-2'-deoxycytidine 5'-monophosphate, either or both of which may be present at a concentration from about 0.1 $\mu$M to about 50 $\mu$M. Alternatively, the cytidine analogue may be 5-aza-2'-deoxycytidine or 5-bromo-2'-deoxycytidine, either of which can further comprise one or more phosphates attached to the 3' and/or 5' carbon(s). The medium may be serum free, and the mammalian cells may be cultured at a temperature from about 29° C. to 36° C. The recombinant protein may be an antibody. The mammalian cells may be CHO cells.

In another aspect, the invention provides a method for producing a recombinant protein comprising culturing CHO cells in a medium comprising 5-aza-2'-deoxycytidine at a concentration from about 0.1 $\mu$M to about 50 $\mu$M at a temperature of less than 37° C., wherein the CHO cells secrete the recombinant protein into the medium and wherein the medium is serum free, and collecting the medium comprising the recombinant protein. Alternatively, the medium can comprise a compound comprising 5-aza-2'-deoxycytidine with one or more phosphate groups attached to its 5' and/or 3' carbon(s).

Further, the invention provides a method for producing a recombinant protein comprising culturing CHO cells in a medium comprising 5-bromo-2'-deoxycytidine 5'-monophosphate at a concentration from about 0.1 $\mu$M to about 50 $\mu$M at a temperature of less than 37° C., wherein the CHO cells secrete the recombinant protein into the medium and wherein the medium is serum free, and collecting the medium comprising the recombinant protein. Alternatively or in addition, the medium can comprise 5-bromo-2'-deoxycytidine without any phosphate groups attached or with one or more phosphate groups attached to its 5' and/or 3' carbon(s).

The invention further comprises an improvement in a method for producing a protein by culturing mammalian cells, wherein the protein is secreted into the medium, comprising growing the mammalian cells in a medium comprising a DNA demethylating agent, whereby the production of the protein is increased. The DNA demethylating agent may be a cytidine analogue and may be present at a concentration from about 0.01 $\mu$M to about 100 $\mu$M. The cytidine analogue may be 5-aza-2'-deoxycytidine, which may have one or more phosphate groups attached to its 5' and/or 3' carbon(s). The mammalian cells may be CHO cells.

In still another aspect, the invention provides a mammalian cell culture comprising a serum free medium comprising 5-aza-2'-deoxycytidine, which may have one or more phosphate groups attached to its 5' and/or 3' carbon(s), at a concentration from about 0.1 $\mu$M to about 50 $\mu$M and a CHO cell line that has been genetically engineered to express a recombinant, secreted protein.

The invention also provides a mammalian cell culture comprising a serum free medium comprising 5-aza-2'-deoxycytidine, which may have one or more phosphate groups attached to its 5' and/or 3' carbon(s), at a concentration from about 0.1 $\mu$M to about 50 $\mu$M and a cell line that can express an antibody.

In still another aspect, the invention provides a mammalian cell culture comprising a medium comprising 5-bromo-2'-deoxycytidine, which may have one or more phosphate groups attached to its 5' and/or 3' carbon(s), at a concentration from about 0.1 $\mu$M to about 50 $\mu$M, wherein the the medium is serum free, and a CHO cell line that has been genetically engineered to express a recombinant, secreted protein.

Finally, the invention includes a mammalian cell culture comprising a medium comprising 5-bromo-2'-deoxycytidine, which may have one or more phosphate groups attached to its 5' and/or 3' carbon(s), at a concentration from about 0.1 µM to about 50 µM, wherein the medium is serum free and a cell line that can express an antibody.

DETAILED DESCRIPTION

An "antibody" is a polypeptide or complex of polypeptides, each of which comprises at least one variable antibody immunoglobulin domain. Antibodies may be single chain antibodies, dimeric antibodies, or some higher order complex of polypeptides including, but not limited to, heterodimeric antibodies.

An "$F_C$ portion of an antibody" includes human or animal immunoglobulin domains $C_H2$ and $C_H3$ or immunoglobulin domains substantially similar to these. For discussion, see Hasemann and Capra, Immunoglobulins: Structure and Function, in William E. Paul, ed., Fundamental Immunology, Second Edition, 209:212–213 (1989).

Cells have been "genetically engineered" to express a specific protein when recombinant nucleic acid sequences that allow expression of the protein have been introduced into the cells using methods of "genetic engineering," such as viral infection, transfection, transformation, transduction, or electroporation. See e.g. Kaufman et al. (1990), Meth. Enzymol. 185:487–511. This can include, for example, the introduction of nucleic acids encoding the protein into the cells or the introduction of regulatory sequences to enhance the expression of a host gene encoding the protein as described in U.S. Pat. No. 5,272,071 to Chappel. The methods of "genetic engineering" further encompass numerous methods including, but not limited to, amplifying nucleic acids using polymerase chain reaction, assembling recombinant DNA molecules by cloning them in *Escherichia coli*, restriction enzyme digestion of nucleic acids, ligation of nucleic acids, in vitro synthesis of nucleic acids, and transfer of bases to the ends of nucleic acids, among numerous other methods that are well-known in the art. See e.g. Sambrook et al., Molecular Cloning: A Laboratory Manual, $2^{nd}$ ed., vol. 1–3, Cold Spring Harbor Laboratory, 1989.

"Growth phase" means a period during which cultured cells are rapidly dividing and increasing in number. During growth phase, cells are generally cultured in a medium and under conditions designed to maximize cell proliferation. Typically in commercial production, protein produced during a growth phase is not harvested for use.

A "multimerization domain" is a domain within a protein molecule that confers upon it a propensity to associate with other protein molecules through covalent or non-covalent interactions.

A "protein" is generally understood to be a polypeptide at least 10 amino acids in length, optionally, at least 15, 20, 25, 30, 35, 40, 50, 60, 70, 80, 90, 100, 125, 150, 175, or 200, amino acids in length. The proteins produced using the methods of the invention can be secreted proteins.

"Production medium" means a cell culture medium designed to be used to culture cells during a production phase.

"Production phase" refers to a period during which cultured cells are producing protein that will be harvested for use. In contrast, protein produced during a growth phase may not be harvested in a typical commercial process. A production phase can be characterized by the use of medium and culture conditions designed to maximize protein production and can sometimes lead to less cell division than a growth phase. The amount of cell division and the productivity of the cells can vary during the course of a production phase. A production phase can be carried out at large scale, that is, in a volume of at least about 100 liters, optionally at least about 500 liters, 1000 liters, 2000 liters, or 5000 liters.

A "recombinant fusion protein" is a fusion of all or part of at least two proteins, which is made using the methods of genetic engineering.

A "recombinant protein," as used herein, is a protein that is expressed as a result of the use of genetic engineering to introduce into host cells nucleic acids encoding the protein and/or nucleic acids that can result in enhanced expression of nucleic acids encoding the protein.

As meant herein, a medium constituent, such as a DNA demethylating agent or a cytidine analogue, "results in" an effect in a culture (such as an increase in the production of a protein) when the effect is observed where mammalian cells are cultured in a medium containing the constituent and is not observed, or is observed to a lesser extent, where the mammalian cells are cultured in a medium lacking the constituent, where the media and conditions are otherwise essentially identical.

"Substantially similar" proteins are at least 80%, optionally at least 90%, identical to each other in amino acid sequence and maintain or alter in a desirable manner the biological activity of the unaltered polypeptide. Conservative substitutions, unlikely to affect biological activity, include the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and these changes in the reverse. See e.g. Neurath et al., *The Proteins*, Academic Press, New York (1979). The percent identity of two amino sequences can be determined by visual inspection and mathematical calculation, or more preferably, the comparison is done by comparing sequence information using a computer program such as the Genetics Computer Group (GCG; Madison, Wis.) Wisconsin package version 10.0 program, 'GAP' (Devereux et al. (1984), Nucl. Acids Res. 12:387) or other comparable computer programs. The preferred default parameters for the 'GAP' program include: (1) the weighted amino acid comparison matrix of Gribskov and Burgess (1986), Nucl. Acids Res. 14:6745, as described by Schwartz and Dayhoff, eds., Atlas of Polypeptide Sequence and Structure, National Biomedical Research Foundation, pp. 353–358 (1979), or other comparable comparison matrices; (2) a penalty of 30 for each gap and an additional penalty of 1 for each symbol in each gap for amino acid sequences; (3) no penalty for end gaps; and (4) no maximum penalty for long gaps. Other programs used by those skilled in the art of sequence comparison can also be used. An alignment of two proteins produced by GAP can span at least about 10, 25, 50, 75, or 100 amino acids.

"Transition phase" means a period of cell culture between a "growth phase" and a "production phase." During transition phase, the medium and environmental conditions are typically shifted from those designed to maximize proliferation to those designed to maximize polypeptide production.

A "variable antibody immunoglobulin domain" is an immunoglobulin domain that is identical or substantially similar to a $V_L$ or a $V_H$ domain of human or animal origin.

Eukaryotic DNA can be, and often is, methylated at the 5 position of a deoxycytidine within the sequence dCpdG, and enzymes that perform this function, called DNA (cytosine C5)methyltransferases (C5 MeTases), have been isolated from numerous eukaryotes. See e.g. Bolden et al. (1984), J. Biol. Chem. 259:12437–43. Prokaryotes can also have C5 MeTases. See e.g. Osterman et al (1988), Biochemistry 27:5204–10. Not surprisingly, inhibition of C5 MeTase has been correlated with demethylation of DNA in cultured cells. Increased cell differentiation and changes in patterns of gene expression have also been observed in connection with inhibition of C5 MeTase. See e.g. Frostesjo et al. (1997), J. Biol. Chem. 272(7):4359–66; Konieczny and Emerson (1984), Cell 38:791–800. Methylation in regulatory regions of a gene can correlate with a repressed state with respect to gene expression. Singal et al. (2001), Cancer Research 61:4820–26.

Two abundant human C5 MeTases have been identified, which are encoded by different splice variants of the Dmntl gene in humans. Hsu et al. (1999), Proc. Natl. Acad. Sci. 96:9751–56. Both comprise an N-terminal domain that is well-conserved among eukaryotic C5 MeTases but not present in prokaryotic C5 MeTases. Yoder et al. (1996), J. Biol. Chem. 271(49):31092–97. Both also comprise a C-terminal domain, which resembles the bacterial C-methylation enzymes. Hsu et al., supra. Numerous sequences of C5-MeTases from various eukaryotes have been reported, which share substantial homologies. See e.g. Bestor et al. (1988), J. Mol. Biol. 203:971–83; Yoder et al., supra; Yen et al. (1992), Nucleic Acids Res. 20:2287–91; Ramchandani et. al. (1998), Biol. Chem. 379:53540; Deng and Szyl (1998), J. Biol. Chem. 273:22869–72; Tajima et al. (1995), J. Biochem. 117.1050–57; and Kimura et al. (1996), J. Biochem. 120:1182–89. As illustrated below, C5 MeTase uses S-adenosylmethionine as a methyl donor, converting it to S-adenosylhomocysteine as it methylates DNA.

Deoxycytidine

5-Methyldeoxycytidine

Frostesjo et al., supra.

Numerous diverse molecules are known to interfere with DNA methylation, either directly or indirectly. Those that can inhibit DNA methylation in cultured cells when added to culture medium are referred to herein as "DNA demethylating agents" or, alternatively may be referred to as a "means for demethylating DNA." Some of these are known to inhibit C5 MeTase directly, for example, by binding to it tightly. See e.g. Sheikhnejad et al. (1999), J. Mol. Biol. 285:2021–34. Some synthetic polynucleotides are powerful inhibitors of C5 MeTases in cultured cells (see e.g. Szyf et al., (1992), J. Biol. Chem. 267(18): 12831–36; U.S. Pat. No. 6,184,211 B1) and thus are DNA demethylating agents as meant herein. In addition, cells grown in medium containing the omnithine carboxylase inhibitor □-difluoromethylornithine accumulate decarboxylated S-adenosylmethionine, which is a competitive inhibitor of C5 MeTase. Frostesjo et al. supra. Such cells undergo changes in the methylation of their genomes and in their state of differentiation. Thus, □-difluoromethyl-ornithine is a DNA demethylating agent as meant herein. Further, molecules that can suppress expression of C5 MeTase, including antisense nucleic acids (such as those described in U.S. Pat. No. 6,184,211 B1 and Szyfet al. (1992), J. Biol. Chem. 267(18):12831–36), ribozymes, interfering RNAs (see e.g. Fjose et al. (2001), Biotechnol. Ann. Rev. 7:31–57), or dibutyryl cyclic AMP (as described by Soultanas et al. (1993), J. Mol. Encocrinol. 11(2): 191–200), are also DNA demethylating agents as meant herein. Benzo(a)pyrene treatment of some cells can result in a decrease in DNA methylation. Wilson and Jones (1983), Cell 32:23946. Benzo(a) pyrene is therefore considered a DNA demethylating agent as meant herein. Finally, L-ethionine can induce differentiation and inhibit DNA methylation when added to the medium of cultured cells without preventing cell division or macromolecular synthesis (Christman et al. (1977), Eur. J. Biochem. 81(1):53–61), and L-ethionine in the form of S-adenosylethionine has been shown to inhibit DNA methylase activity from Novikoff hepatoma (Sneider et al. (1975), Nucleic Acids Res. 2:1685–1799). These molecules are also encompassed within what is considered herein to be DNA demethylating agents.

Various cytidine analogues are DNA demethylating agents. See e.g. Jones and Taylor (1980), Cell 20:85–93. Some cytidine analogues have been shown to interact with C5 MeTase directly by binding to it tightly or irreversibly. See Wu and Santi (1985), Prog. Clin. Biol. Res. 198:199–29; Sheikhnejad et al. (1999), J. Mol. Biol, 285:2021–34. For the purposes of this invention, "cytidine analogues" include, but are not limited to, molecules described below with reference to structures A through H.

STRUCTURE A

STRUCTURE B

STRUCTURE C

STRUCTURE D

STRUCTURE E

STRUCTURE F

STRUCTURE G

STRUCTURE H

In Structure A, X can be OH (to yield, for example, 5-azacytidine) or H (to yield, for example, 5-aza-2'-deoxycytidine, which is also called decitabine). In Structure B, X can be OH (to yield, for example, 5,6-dihydro-5-azacytidine) or H (to yield, for example, 5, 6-dihydro-5-aza-2'-deoxycytidine). In Structure C, X can be OH or H, and Y can be fluorine (to yield, for example, 5-fluorocytidine or 5-fluoro-2'-deoxycytidine), chlorine, bromine (to yield, for example, 5-bromocytidine, 5-bromo-2'-deoxycytidine, or 5-bromo-2'-deoxycytidine 5'-monophosphate), iodine, a trifluoromethyl group (to yield, for example, 5-trifluoromethylcytidine or 5-trifluoromethyl-2'-deoxycytidine), a trichloromethyl group, a tribromomethyl group, or a triiodomethyl group. In Structure D, X can be OH (to yield, for example, pseudoisocytidine) or H. In Structure E, X can be H (to yield, for example, 6-aza-2'-deoxycytidine) or OH (to yield, for example, 6-azacytidine). In Structure F, X can be OH (to yield, for example, 5,6-dihydro-6-azacytidine) or H. In Structure G, X can be H or OH, and Y can be fluorine (to yield, for example, 6-fluorocytidine or 6-fluoro-2'-deoxycytidine), chlorine, bromine (to yield, for example, 6-bromocytidine or 6-bromo-2'-deoxycytidine), iodine, a trifluoromethyl group (to yield, for example, 6-trifluoromethylcytidine or 6 trifluoromethyl-2'-deoxycytidine), a trichloromethyl group, a tribromomethyl group, or a triiodomethyl group. In Structure H, X can be OH or H, and R can be an unaltered cytosine ring or any of the altered cytosine rings described with reference to Structures A through G. Further, in any of Structures A to H, Z can be a hydroxyl group or one or more phosphate groups, and W can be a hydroxyl group or one or more phosphate groups.

Other DNA demethylating agents include oligonucleotides such as those described in U.S. Pat. Nos. 6,268,137 B1 and 5,503,975, International Patent Application WO 99/12027, and Sheikhnejad et al. (1999), J. Mol. Biol. 285:2021–34. Further, an agent that can enhance DNA demethylase activity (see U.S. Pat. No. 6,184,211) can be a DNA demethylating agent as meant herein. Moreover, DNA demethylating agents include polynucleotides comprising the sequence ZpG, where Z is any of the cytidine analogues deoxyribonucleotide, and where the ZpG is base paired to a CpG sequence on the same or a different polynucleotide molecule. Such oligonucleotides can be more effective as inhibitors if the cytidine in this CpG sequence is methylated. Some such polynucleotides are described in Osterman et al. (1988), Biochemistry 27:5204–10.

To determine whether a particular molecule is a DNA demethylating agent, numerous assays are known in the art. As meant herein, the presence of a DNA demethylating agent in mammalian cell culture medium can result in a decrease in DNA methylation in the cells (relative to a control culture grown without the DNA demethylating agent). Jones and Taylor ((1980), Cell 20:85–93) describe three assays for comparing the extent of DNA methylation. One of these methods includes; (1) radioactive labeling of living cultured cells with $^{14}$C-thymidine and methyl-$^3$H-methionine; (2) subsequent isolation of DNA; (3) hydrolysis of the DNA, (4) separation of the nucleotides of the hydrolyzed DNA on cellulose plates; (5) determination of the ratio between the $^{14}$C and $^3$H isotopes; and (6) comparison of the ratios obtained in cells grown without a DNA demethylating agent or grown with varying concentrations of a DNA demethylating agent. In more detail, as described in Jones and Taylor (supra), cultured mammalian cells from a log phase culture can be seeded in 35 mm dishes at about $10^5$ cells per dish in the presence or absence of a DNA demethylating agent. After 8 hours of incubation at about 37° C., 2 $\mu$Ci/ml methyl-$^3$H-methionine (>100 mCi/mmole), 0.01 $\mu$Ci/ml 2-$^{14}$C-thymidine (about 50 $\mu$Ci/rmnole), and 10 $\mu$M sodium formate can be added, and the cultures can be incubated at about 37° C. for an additional 16 hours. The cells can then be washed in saline, resuspended in 1 ml of 0.3 M NaOH containing 0.5% sodium dodecylsulfate, and incubated for 24 hours at 37° C. The suspension can then be neutralized with 0.15 ml of 2 M HCl and 0.35 ml of 0.5 M Tris-HCl (pH 7.6). Proteinase K can be added to a concentration of 0.1 mg/ml, and the suspension can be incubated for an additional 24 hours at 37° C. The cell lysate can be transferred to a test tube. DNA can be precipitated by adding 200 $\mu$l of 50% trichloroacetic acid and 10 $\mu$g of salmon DNA (as carrier) and allowing the tubes to stand at room temperature for 15 minutes. The precipitate can be collected by centrifugation at 1000×g for 20 minutes, washed with 96% ethanol, dried under vacuum, and hydrolyzed in 100 $\mu$l of 70% perchloric acid at 60° C. overnight. Phenol red can be added, and the hydrolysates can be neutralized with 5 M KOH. The potassium perchlorate precipitate can be removed by centrifugation after incubation for 15 minutes on ice. An aliquot of the supernatant (about 100 $\mu$l) can be applied to a cellulose plate along with 5-methylcytosine (as carrier). The plates can be developed in isopropanol:HCl:H$_2$O (65:16.7:18.3, v/v), and the spots for thymine and 5-methylcytosine can be located under ultraviolet light, scraped off the plates, and extracted overnight with 1 ml of 0.1 M HCl at 37° C. The extracted radioactivity can be counted in a scintillation counter in an appropriate scintillation fluid using window settings for double label counting.

As described herein, a method for producing a protein in cultured cells is provided, which comprises adding a DNA demethylating agent, optionally a cytidine analogue such as those described above, to the culture medium and culturing the cells at either normal or hypothermic temperatures. The DNA demethylating agent may be part of the starting medium or may be added to the culture in one or more feeds at later times In particular embodiments, addition of 5-aza-2'-deoxycytidine (also called decitabine) or 5-bromo-2'-deoxycytidine 5'-monophosphate to a mammalian cell culture can enhance recombinant protein production at either 37° C. or at a lower temperature, such as from about 29° C. to about −36° C. or from about 29° C. to about 35° C. As is known in the art, different temperatures and/or different media may be appropriate for different kinds of cells or for different cell lines. This method can be used along with other methods known in the art for increasing the quantity or quality of protein produced by cultured cells. A DNA demethylating agent can be added to the culture medium once or, optionally, more than once. Multiple additions may be appropriate when, for example, a DNA demethylating agent is unstable under the culture conditions.

A cytidine analogue can be present in culture medium, which may be growth medium or production medium, at a concentration from about 0.01 $\mu$M to about 300 $\mu$M, optionally from about 0.05 $\mu$M to about 100 $\mu$M, from about 0.1 $\mu$M to about 50 $\mu$M, from about 1 $\mu$M to about 20 $\mu$M, or at about 10 $\mu$M. An oligonucleotide DNA demethylating agent can be present at a concentration from about 10 nanomolar (nM) to about 100 $\mu$M, optionally from about 0.1 $\mu$M to about 10 $\mu$M. The cytidine analog or DNA demethylating agent can be part of the medium initially or can be added to a culture at one or more later times, optionally during a production phase of the culture. Optionally, a cationic liposome reagent such as, for example, LIPOFECTIN™ (a 1:1 formulation of N-[1-(2,3-dioleyloxy)propyl]-n,n,n-trimethylammonium chloride (DOTMA) and dioleoyl phosphotidylethanolamine (DOPE) in membrane filtered water) can also be present to facilitate cellular uptake of the oligonucleotide. The method can be particularly appropriate for the large scale (that is, in volumes of at least about 100 liters) production of recombinant proteins that are secreted into the culture medium in cultured mammalian cells, but can also be used in small scale cultures to produce nonrecombinant proteins that are not secreted.

In one aspect, the invention provides a method for culturing mammalian cells in a volume of at least about 100 liters comprising growing in culture a mammalian cell, especially a CHO cell that has been genetically engineered to produce a protein, and adding to the culture a DNA demethylating agent, especially 5-aza-2'-deoxycytidine and/or 5-bromo-2'-deoxycytidine 5'-monophosphate. One kind of genetically engineered cell is a cell that has been transformed, transfected, and/or transduced with a recombinant vector encoding the protein. The protein can be expressed under the control of a heterologous promoter, for example, a viral promoter, such as a cytomegalovirus, a polyoma virus, an adenovirus, or a simian virus 40 promoter or a promoter derived from mammalian cells such as a metallothionine promoter, a ☐actin promoter, or a ☐globin promoter Typically, the cell does not naturally express the protein or expresses the protein only at very low levels in the absence of genetic engineering. In some embodiments, the protein can be secreted into the medium, from which it can be recovered.

Particularly preferred proteins for expression are protein-based drugs, also known as biologics. Preferably, the proteins are secreted as extracellular products. The protein being produced can comprise part or all of a protein that is identical or substantially similar to a naturally-occurring protein, and/or it may, or may not, be a recombinant protein and/or a recombinant fusion protein. Optionally, the protein may be a human protein, a fragment thereof, or a substantially similar protein that is at least 15 amino acids in length. It may comprise a non-antibody protein and/or an antibody. It may be produced intracellularly or be secreted into the culture medium from which it can be recovered. It may or may not be a soluble protein.

The methods of the invention can be used to increase the production of just about any protein, and is particularly advantageous for proteins whose expression is under control of a strong promoter, such as, for example, a viral promoter or a metallothionine promoter, and/or proteins that are encoded on a message that has an adenoviral tripartite leader element (see e.g. Logan and Shenk (1984), Proc. Natl. Acad. Sci. 81(12):3655–59), an internal ribosome entry sequence (see e.g. Vagner et al. (2001), EMBO Rep. 2(10):893–98), or an Expression Augmenting Sequence Element (EASE; see U.S. Pat. No. 6,027,915). Examples of useful expression vectors that can be used to produce proteins are those disclosed in WO 01/27299, the pDC409 vector described in McMahan et al. ((1991), EMBO J. 10:2821), the pDC312 or pDC214 vectors, which are similar to pG3.6 described in Morris et al. ((1998), Cytotechnology 28:9–17), and the pDSR□2 vector described in International Application No. WO 90/14363. A protein is generally understood to be a polypeptide of at least about 10 amino acids, optionally at least about 25, 50, 75, or 100 amino acids.

Proteins that can be produced with the methods of the invention include those comprising amino acid sequences identical to or substantially similar to all or part of one of the following proteins: a Flt3 ligand (as described in International Application No. WO 94/28391), a CD40 ligand (as described in U.S. Pat. No. 6,087,329), erythropoeitin, thrombopoeitin, calcitonin, leptin, IL-2, angiopoietin-2 (as described by Maisonpierre et al. (1997), Science 277(5322) :55–60), Fas ligand for receptor activator of NF-kappa B (RANKL, as described in International Application No. WO 01/36637), tumor necrosis factor (TNF)-related apoptosis-inducing ligand (TRAIL, as described in International Application No. WO 97/01633), thymic stroma-derived lymphopoietin, granulocyte colony stimulating factor, granulocyte-macrophage colony stimulating factor (GM-CSF, as described in Australian Patent No. 588819), mast cell growth factor, stem cell growth factor (described in e.g. U.S. Pat. No. 6,204,363), epidermal growth factor, keratinocyte growth factor, megakaryote growth and development factor, RANTES, growth hormone, insulin, insulinotropin, insulin-like growth factors, parathyroid hormone, interferons including Li interferons, □interferon, and consensus interferons (such as those described in U.S. Pat. Nos. 4,695,623 and 4,897,471, nerve growth factors, brain-derived neurotrophic factor, synaptotagmin-like proteins (SLP 1–5), neruotrophin-3, glucagon, interleukins 1 through 18, colony stimulating factors, lymphotoxin-□, tumor necrosis factor (TNF), leukemia inhibitory factor, oncostatin-M, and various ligands for cell surface molecules ELK and Hek (such as the ligands for eph-related kinases or LERKS). Descriptions of proteins that can be produced according to the inventive methods may be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991).

Further proteins that can be produced using the methods of the invention include proteins comprising all or part of the amino acid sequence of a receptor for any of the above-mentioned proteins, an antagonist to such a receptor, or proteins substantially similar to such receptors or antagonists. These receptors and antagonists include: both forms of tumor necrosis factor receptor (TNFR, referred to as p55 and p75, as described in U.S. Pat. No. 5,395,760 and U.S. Pat. No. 5,610,279), Interleukin-1 (IL-1) receptors (types I and II; described in EP Patent No. 0 460 846, U.S. Pat. No. 4,968,607, and U.S. Pat. No. 5,767,064), IL-1 receptor antagonists (such as those described in U.S. Pat. No. 6,337,072), IL-1 antagonists or inhibitors (such as those described in U.S. Pat. Nos. 5,981,713, 6,096,728, and 5,075,222), IL-2 receptors, IL-4 receptors (as described in EP Patent No. 0 367 566 and U.S. Pat. No. 5,856,296), IL-15 receptors, IL-17 receptors, IL-18 receptors, granulocyte-macrophage colony stimulating factor receptor, granulocyte colony stimulating factor receptor, receptors for oncostatin-M and leukemia inhibitory factor, receptor activator of NF-kappa B (RANK, described in WO 01/36637 and U.S. Pat. No. 6,271,349), osteoprotegrin (described in e.g. U.S. Pat. No. 6,015,938), receptors for TRAIL (including TRAIL receptors 1, 2, 3, and 4), and receptors that comprise death domains, such as Fas or Apoptosis-Inducing Receptor (AIR).

More proteins that can be produced using the methods of the invention include proteins comprising all or part of the amino acid sequences of differentiation antigens (referred to as CD proteins) or their ligands or proteins substantially similar to either of these. Such antigens are disclosed in *Leukocyte Typing VI(Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand. Accordingly, members of the TNF and TNFR families can also be produced using the present invention.

Enzymatically active proteins or their ligands can also be produced using the methods of the invention. Examples include proteins comprising all or part of one of the following proteins or their ligands or a proteins substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-1, globins, an IL-2 antagonist, alpha-I antitrypsin, TNF-alpha Converting Enzyme, ligands for any of the above-mentioned enzymes, and numerous other enzymes and their ligands.

The methods of the invention can also be used to produce proteins that are antibodies or portions thereof and chimeric antibodies, e.g. antibodies having human constant antibody immunoglobulin domains coupled to one or more murine variable antibody immunoglobulin domain, fragments thereof, or substantially similar proteins. The method of the invention may also be used to produce conjugates comprising an antibody and a cytotoxic or luminescent substance. Such substances include: maytansine derivatives (such as DM1); enterotoxins (such as a *Staphlyococcal* enterotoxin); iodine isotopes (such as iodine-125); technetium isotopes (such as Tc-99m); cyanine fluorochromes (such as Cy5.5.18); and ribosome-inactivating polypeptides (such as bouganin, gelonin, or saporin-S6). The invention can also be used to produce chimeric proteins selected in vitro to bind to a specific target protein and modify its activity such as those described in International Applications WO 01/83525 and WO 00/24782, both of which are incorporated by reference. Examples of antibodies, in vitro-selected chimeric proteins, or antibody/cytotoxin or antibody/lumninophore conjugates that can be produced by the methods of the invention include those that recognize any one or a combination of polypeptides including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1□, IL-1□, IL-2, IL-3, IL-7, IL-4, IL-5, IL-8, IL-10, IL-2 receptor, IL-4 receptor, IL-6 receptor, IL-13 receptor, IL-18 receptor subunits, PDGF-□ and analogs thereof (such as those described in U.S. Pat. Nos. 5,272,064 and 5,149,792), VEGF, TGF, TGF-□2, TGF-□, EGF receptor (including those described in U.S. Pat. No. 6,235,883 B1, incorporated by reference) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19–25), C5 complement, IgE, tumor antigen CA 125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or polypeptides expressed on breast, colon, squamous cell, prostate, pancreatic, lung, and/or kidney cancer cells and/or on melanoma, glioma, or neuro-blastoma cells, the necrotic core of a tumor, integrin alpha 4 beta 7, the integrin VLA-4, B2 integrins, TRAIL receptors 1, 2, 3, and 4, RANK, RANK ligand, TNF-□, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC 1, carcinoembryonic antigen (CEA), alpha-fetoprotein (AFP), tumor necrosis factor (TNF), CTLA4 (which is a cytotoxic T lymphocyte-associated antigen), Fc-□-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*.

The invention may also be used to produce all or part of an anti-idiotypic antibody or a substantially similar polypeptide, including anti-idiotypic antibodies against: an antibody targeted to the tumor antigen gp72; an antibody against the ganglioside GD3; an antibody against the ganglioside GD2; or antibodies substantially similar to these.

The methods of the invention can also be used to produce recombinant fusion proteins comprising all or part of any of the above-mentioned proteins. For example, recombinant fusion proteins comprising one of the above-mentioned proteins plus a multimerization domain, such as a leucine zipper, a coiled coil, an Fc portion of an antibody, or a substantially similar protein, can be produced using the methods and media of the invention. See e.g. International Application No. WO 94/10308; Lovejoy et al. (1993), Science 259:1288–1293; Harbury et al. (1993), Science 262: 1401–05; Harbury et al. (1994), Nature 371:80–83; Håkansson et al.(1999), Structure 7:255–64. Specifically included among such recombinant fusion proteins are proteins in which TNFR or RANK is fused to an Fc portion of an antibody (TNFR:Fc or RANK:Fc). TNFR:Fc comprises the Fc portion of an antibody fused to an extracellular domain of TNFR, which includes amino acid sequences substantially similar to amino acids 1–163, 1–185, or 1–235 of FIG. 2A of U.S. Pat. No. 5,395,760. RANK:Fc is described in International Application No. WO 01/36637.

Suitable cells for practicing the present invention include any cell line, optionally a mammalian cell line that has been genetically engineered to express a protein, although the invention can also be used to produce non-recombinant proteins. Optionally, the cells can be clonal cell lines. Numerous suitable cell lines are known in the art. For example, Chinese hamster ovary (CHO), HeLa, VERO, BHK, Cos, MDCK, 293, 3T3, myeloma (e.g. NSO, NSI), HT-1080, or W138 cells may be used. Hybridoma or myeloma cell lines that produce an antibody can be used to practice the invention. In this case, the mRNA encoding the antibody can be transcribed from an endogenous promoter. Cell lines derived from the above-mentioned cells are also suitable for practicing the invention.

CHO cells are widely used for the production of recombinant proteins, e.g. cytokines, clotting factors, and antibodies, and are contemplated for use in practicing the methods of the invention. Brasel et al. (1996), Blood 88: 2004–2012; Kaufman et al. (1988), J. Biol. Chem. 263:6352–6362; McKinnon et al. (1991), J Mol Endocrinol 6:231–239; Wood et al. (1990), J. Immunol 145:3011–3016. A dihydrofolate reductase (DHFR)-deficient mutant cell line (Urlaub et al. (1980), Proc. Natl. Acad. Sci. USA 77:4216–4220), such as DXB11 or DG-44, is useful because the efficient DHFR selectable and amplifiable gene expression system allows high level recombinant protein expression in these cells (Kaufman (1990), Meth. Enzymol. 185:527–566). In addition, these cells are easy to manipulate as adherent or suspension cultures and exhibit relatively good genetic stability. CHO cells and recombinant proteins expressed in them have been extensively characterized and have been approved for use in clinical commercial manufacturing by regulatory agencies.

According to the present invention, a mammalian host cell is cultured under conditions that promote the production of the protein of interest, which can be an antibody or a recombinant protein. Cell culture medium formulations are well known in the art. Suitable commercial media include RPMI 1641 Medium, Dulbecco's Modified Eagle's Medium, Minimal Essential Medium Eagle, F-12K and F12 Medium, McCoy's 5A Medium, Leibovitz's L-15 Medium, which can be obtained from the American Type Culture Collection or JRH Biosciences as well as other vendors, and serum-free media such as EX-CELL™ 300 Series (especially EX-CELL™ 325 PF CHO Protein-Free Medium) available from JRH Biosciences, Lenexa, Kans., USA) or CD CHO Medium (a serum-free, protein-free medium available from GIBCO™ Invitrogen Corporation), among others. To these culture medium formulations the skilled artisan will add components such as amino acids, salts, sugars, vitamins, hormones, growth factors, buffers, antibiotics, lipids, trace elements and the like, depending on the requirements of the host cells to be cultured.

The skilled artisan may also choose to use one of the many individualized media formulations that have been developed to maximize cell growth, cell viability, and/or recombinant polypeptide production in a particular cultured host cell. The methods according to the current invention may be used in combination with commercially available cell culture media or with a cell culture medium that has been individually formulated for use with a particular cell line. For example, an enriched medium that could support increased polypeptide production may comprise a mixture of two or more commercial media, such as, for instance, DMEM and Ham's F12 media combined in ratios such as, for example, 1:1, 1:2, 1:3, 1:4, 1:5, 1:6, 1:7, 1:8, or even up to 1:15 or higher. Alternatively or in addition, a medium can be enriched by the addition of nutrients, such as amino acids or peptone, and/or a medium (or most of its components with the exceptions noted below) can be used at greater than its usual, recommended concentration, for example at 2×, 3×, 4×, 5×, 6×, 7×, 8×, or even higher concentrations. As used herein, "1×" means the standard concentration, "2×" means twice the standard concentration, etc. In any of these embodiments, medium components that can substantially affect osmolarity, such as salts, cannot be increased in concentration so that the osmolarity of the medium falls outside of a range conducive to maintaining cell viability. Thus, a medium may, for example, be 8× with respect to all components except salts, which may be present at only about 1×. A medium may contain serum or may be serum free, protein free, or chemically defined. A medium may, on the other hand, contain serum or proteins such as, for example, insulin or IGF-1. Protein hydrolyzates, such as, for example, yeast peptones or soy protein hydrolyzates, are not proteins as meant by the term "protein free medium." Further, a medium may be supplemented periodically during the time a culture is maintained to replenish medium components that can become depleted such as, for example, vitamins, amino acids, and metabolic precursors. As is known in the art, different media and temperatures may have somewhat different effects on different cell lines, and the same medium and temperature may not be suitable for all cell lines.

The methods of the invention are useful for inducing the production of recombinant proteins. In some embodiments, a recombinant polynucleotide molecule introduced into a cell to alter the expression of a certain protein comprises nucleic acids encoding the protein of interest operably linked to suitable regulatory sequences, which are part of an "expression vector" into which the nucleic acids encoding the protein of interest are inserted.

Methods and vectors for genetically engineering cells and/or cell lines to express a protein of interest are well known to those skilled in the art; for example, various techniques are illustrated in *Current Protocols in Molecular Biology*, Ausubel et al., eds. (Wiley & Sons, New York, 1988, and quarterly updates); Sambrook et al., *Molecular Cloning: A Laboratory Manual* (Cold Spring Laboratory Press, 1989) and Kaufman, R. J., *Large Scale Mammalian Cell Culture* (1990, pp. 15–69). Additional protocols using commercially available reagents, such as the cationic lipid reagents LIPOFECTAMINE™, LIPOFECTAMINE™-2000, or LIPOFECTAMINE™-PLUS (which can be purchased from Invitrogen), can be used to transfect cells. Felgner et al. (1987), Proc. Natl. Acad. Sci. USA 84:7413–7417. In addition, electroporation or bombardment with microprojectiles coated with nucleic acids can be used to transfect cells using procedures, such as those in Sambrook et al., *Molecular Cloning: A Laboratory Manual*, 2nd ed. Vol. 1–3 (Cold Spring Harbor Laboratory Press, 1989) and Fitzpatrick-McElligott ((1992), Biotechnology (NY) 10(9):1036–40). Genetic engineering techniques include, but are not limited to, transfection, transformation, and/or transduction of cells with expression vectors, targeted homologous recombination and gene activation (see e.g. U.S. Pat. No. 5,272,071 to Chappel), and transactivation by engineered transcription factors (see e.g. Segal et al. (1999), Proc. Natl. Acad. Sci. USA 96(6):2758–63).

A gene encoding a selectable marker is often used to facilitate the identification of recombinant cells and is therefore often included in expression vectors. Selection of transformants can be performed using methods such as, for example, the dihydrofolate reductase (DHTR) selection scheme or resistance to cytotoxic drugs. Kaufman et al. (1990), Meth. in Enzymology 185:487–511. A suitable cell line for DHFR selection can be, for example, CHO line DX-B 11, which is deficient in DHFR. Urlaub and Chasin (1980), *Proc. Natl Acad. Sci. USA* 77:4216–4220. Other examples of selectable markers include those conferring resistance to antibiotics, such as G418 and hygromycin B.

The regulatory sequences are typically derived from mammalian, microbial, viral, and/or insect genes. Examples of regulatory sequences include transcriptional promoters, operators, and enhancers, ribosome binding sites (see e.g. Kozak (1991), J. Biol. Chem. 266:19867–70), sequences that can control transcriptional and translational termination, polyadenylation signals (see e.g. McLauchlan et al. (1988), Nucleic Acids Res. 16:5323–33), and matrix and scaffold attachment sites (see Phi-Van et al. (1988), Mol. Cell. Biol. 10:2302–07; Stief et al. (1989), Nature 341:342–35; Bonifer et al. (1990), EMBO J. 9:2843–38). Nucleotide sequences are operably linked when the regulatory sequence functionally relates to the protein coding sequence. Such sequences can be present in cis or in trans as long as they functionally relate to the protein-coding sequence. Thus, a promoter nucleotide sequence is operably linked to a protein coding sequence if the promoter nucleotide sequence controls the transcription of the coding sequence. Although many sequences capable of regulating expression, such as promoters, exert their effects when present in cis, this need not always be the case. For example, non-coding RNAs present in trans may downregulate or enhance gene expression. See e.g. Storz (2002), Science 296: 1260–63.

Some commonly used promoter and enhancer sequences are derived from viral genomes, for example polyoma virus, adenovirus 2, simian virus 40 (SV40), and human cytomegalovirus. For example, the human CMV promoter/enhancer of immediate early gene 1 may be used. See e.g. Patterson et al. (1994), Applied Microbiol. Biotechnol. 40:691–98. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can optionally also contain a viral origin of replication (Fiers et al. (1978), Nature 273:113; Kaufman (1990), Meth. in Enzymol. 185:487–511). Smaller or larger SV40 fragments can also be used.

A sequence encoding an appropriate native or heterologous signal peptide (leader sequence) can be incorporated into an expression vector, to promote extracellular secretion of the recombinant protein. The choice of signal peptide or leader depends on the type of host cells in which the recombinant protein is to be produced, and a heterologous signal peptide can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al. ((1984), Nature 312:768); the interleukin4 receptor signal peptide described in EP Patent No. 0 367 566; the type I interleukin-1 receptor signal peptide described in U.S. Pat. No. 4,968,607; the type II interleukin-1 receptor signal peptide described in EP Patent No. 0 460 846; the signal sequence of human IgK (which is METDTLLLWVLLLWVPGSTG); and the signal sequence of human growth hormone (MATGSRTSLLLAFGLLCLPWLQEGSA).

Additional control sequences shown to improve expression of heterologous genes from mammalian expression vectors include such elements as the expression augmenting sequence element (EASE) derived from CHO cells (Morris et al., in Animal Cell Technology, pp. 529–534 (1997); U.S. Pat. No. 6,312,951 B 1; U.S. Pat. No. 6,027,915; U.S. Pat. No. 6,309,841 B 1) and the tripartite leader (TPL) and VA gene RNAs from Adenovirus 2 (Gingeras et al. (1982), J. Biol. Chem. 257:13475–13491). Internal ribosome entry site (IRES) sequences of viral origin that allow dicistronic mRNAs to be translated efficiently (Oh and Sarnow (1993), Current Opinion in Genetics and Development 3:295–300; Ramesh et al. (1996), Nucleic Acids Research 24:2697–2700). Expression of a heterologous cDNA as part of a dicistronic mRNA followed by the gene for a selectable marker (e.g. DHFR) has been shown to improve transfectability of the host and expression of the heterologous cDNA (Kaufman et al. (1990), Methods in Enzymol. 185:487–511). Exemplary expression vectors that employ dicistronic mRNAs are pTR-DC/GFP described by Mosser et al. ((1997), Biotechniques 22: 150–161) and p2A51 described by Morris et al. ((1997), in *Animal Cell Technology*, pp. 529–534).

A useful high expression vector, pCAVNOT, has been described by Mosley et al. (1989), *Cell* 59:335–348. Other expression vectors for use in mammalian host cells can be constructed as disclosed by Okayama and Berg ((1983) Mol. Cell. Biol. 3:280). A useful system for stable high level expression of mammalian cDNAs in C127 murine mammary epithelial cells can be constructed substantially as described by Cosman et al. ((1986) Mol. Immunol. 23:935). A useful high expression vector, pMLSV N1/N4, described by Cosman et al. ((1984), Nature 312: 768), has been deposited as ATCC 39890. Additional useful mammalian expression vectors are described in EP Patent No. A 0 367 566, WO 01/27299 A1, and Morris et al. ((1998), Cytotechnology 28: 9–17). The vectors can be derived from retroviruses, such as, for example; murine leukemia virus or spleen necrosis virus, adenoviruses, and/or lentiviruses, such as, for example, human immunodeficiency virus. Examples of retroviral vectors include pLNCX, pLCNX, pLZRS, pBMN, pMSCV, pBABE, and pFB. Examples of lentiviral vectors include pHR'-CS, pFUGW, pRRL, and pLENTI.

Suitable culture conditions for mammalian cells are known in the art. See e.g. Animal cell culture: A Practical Approach, D. Rickwood, ed., Oxford University Press, New York (1992); Freshney, Culture of Animal Cells: A Manual of Basic Technique, Wiley-Liss, Inc. (1987). Mammalian cells may be cultured in suspension or while attached to a solid substrate. Furthermore, mammalian cells may be cultured, for example, in fluidized bed, hollow fiber, packed bed, stirred tank, or fibrous bed bioreactors or in roller bottles or shake flasks, with or without microcarriers. Any of these can be operated in a batch, fed batch, continuous, semi-continuous, or perfusion mode. The methods of the invention can be combined with other methods or medium additives, especially those that increase production or sialylation of a protein. For example, cells can be grown at temperatures from about 29° C. to about 40° C., optionally from about 29° C. to about 37° C., from about 29° C. to about 36° C., from about 29° C. to about 35° C., or from about 30° C. to about 33° C. Moreover, substances other than DNA demethylating agents can be added to the medium. Such substances include, but are not limited to, histone deacetylase inhibitors, butyrate, and trichostatin.

The methods according to the present invention may be used to increase the production of proteins in both single phase and multiple phase culture processes. In a single phase process, cells are inoculated into a culture environment, and the disclosed methods and media are employed during the single production phase. In a multiple stage process, cells are cultured in two or more distinct phases. For example, cells may be cultured first in a growth phase, under environmental conditions that maximize cell proliferation and viability, then transferred to a production phase, under conditions that increase the quantity or quality of a protein. The growth and production phases may be preceded by, or separated by, one or more transition phases. In multiple phase processes the methods of the present invention are employed at least during part of the production phase, but may also be employed for all or part of the growth and/or transition phases. A production phase can last days, weeks, or months. Optionally, a production phase lasts from 2 to 40 days, from 5 to 28 days, or from 8 to 12 days.

The examples presented below are not intended to be exhaustive or to limit the scope of the invention. The skilled artisan will understand that modifications and variations are possible in light of the above teachings, and such modifications and variations are intended to be within the scope of the invention. All references cited herein, both supra and infra, are incorporated herein in their entirety.

EXAMPLE 1

Induction of Cells at 31° C. or 34° C.

The following experiment was designed to test whether decitabine can induce the production of a protein, in this case a recombinant soluble form of the human interleukin 1 receptor type II (IL-1-R-II), at either 31° C. or 34° C. Soluble versions of IL-1R-II and methods for producing it are described in U.S. Pat. No. 5,767,064. DNA encoding a soluble form of the human IL-1R-II was inserted into pG3.6, which is described in Morris et al. ((1998), Cytotechnology 28:9–17). This construct was used to transfect CHO cells to produce cell lines, including 25H9, that produce IL-1R-II protein.

About $2 \times 10^6$ cells of cell line 25H9 were inoculated into 30 milliliters of serum-free medium and incubated at the temperatures indicated in Table 1 in vented shake flasks. At the times indicated in Table 1, samples were taken from each flask to determine IL-1R-II titer, cell number, and cell viability. IL-1R-II protein titer was determined by ELISA assay. Cell number was determined by counting cells in a hemocytometer. Cell viability was determined by trypan blue staining and counting stained cells in a hemocytometer. Cumulative viable cell density (CVCD) is the area under the curve of a plot of the viable cell density versus time (in units of cells/ml/day). Productivity (pg of IL-1R-II/cell/day) was determined by dividing the protein titer on a particular day by the CVCD on the same day. Cells were fed with amino acids on days 2 and 5, and dextrose was added periodically in order to maintain levels above 2.0 g/L. All samples were done in duplicate, and the data shown is an average value. Data is shown in Table 1.

TABLE 1

| Temperature/Inducer | Day | Viable Cell Density ($\times 10^6$/ml) | Cumulative Viable Cell Density ($\times 10^6$/ml/day) | Viability (%) | IL-1R-II Titer (μg/ml) | Productivity (pg IL-1R-II/cell/day) |
|---|---|---|---|---|---|---|
| 31° C./No inducer | 0 | 1.8 | 0.0 | 96.1 | 0.0 | — |
| 31° C./No inducer | 3 | 3.3 | 7.8 | 93.8 | 55.7 | 7.2 |
| 31° C./No inducer | 5 | 5.5 | 16.6 | 97.2 | 157.0 | 9.4 |
| 31° C./No inducer | 7 | 6.8 | 29.0 | 94.2 | 159.5 | 5.5 |

TABLE 1-continued

| Temperature/Inducer | Day | Viable Cell Density (×10⁶/ml) | Cumulative Viable Cell Density (×10⁶/ml/day) | Viability (%) | IL-1R-II Titer (µg/ml) | Productivity (pg IL-1R-II/cell/day) |
|---|---|---|---|---|---|---|
| 31° C./No inducer | 10 | 3.6 | 44.5 | 41.9 | 222.0 | 5.0 |
| 31° C./1 µM decitabine | 0 | 1.8 | 0.0 | 96.1 | 0.0 | — |
| 31° C./1 µM decitabine | 3 | 3.7 | 8.3 | 93.4 | 62.6 | 7.5 |
| 31° C./1 µM decitabine | 5 | 5.0 | 17.0 | 94.8 | 132.0 | 7.8 |
| 31° C./1 µM decitabine | 7 | 5.7 | 27.7 | 87.7 | 216.5 | 7.8 |
| 31° C./1 µM decitabine | 10 | 5.1 | 43.8 | 63.9 | 330.5 | 7.5 |
| 31° C./5 µM decitabine | 0 | 1.8 | 0.0 | 96.1 | 0.0 | — |
| 31° C./5 µM decitabine | 3 | 3.8 | 8.5 | 93.6 | 77.8 | 9.2 |
| 31° C./5 µM decitabine | 5 | 3.5 | 15.7 | 84.6 | 123.5 | 7.8 |
| 31° C./5 µM decitabine | 7 | 3.6 | 22.8 | 77.7 | 210.5 | 9.2 |
| 31° C./5 µM decitabine | 10 | 7.8 | 40.0 | 58.5 | 351.0 | 8.8 |
| 31° C./10 µM decitabine | 0 | 1.8 | 0.0 | 96.1 | 0.0 | — |
| 31° C./10 µM decitabine | 3 | 3.1 | 7.4 | 94.5 | 59.1 | 8.0 |
| 31° C./10 µM decitabine | 5 | 3.9 | 14.4 | 80.8 | 149.5 | 10.4 |
| 31° C./10 µM decitabine | 7 | 3.3 | 21.5 | 72.5 | 224.5 | 10.4 |
| 31° C./10 µM decitabine | 10 | 3.6 | 31.8 | 50.6 | 378.0 | 11.9 |
| 34° C./No inducer | 0 | 1.8 | 0.0 | 96.1 | 0.0 | — |
| 34° C./No inducer | 3 | 7.6 | 14.2 | 97.8 | 60.3 | 4.2 |
| 34° C./No inducer | 5 | 15.6 | 37.5 | 86.5 | 134.5 | 3.6 |
| 34° C./No inducer | 7 | 4.9 | 57.9 | 23.5 | 138.0 | — |
| 34° C./1 µM decitabine | 0 | 1.8 | 0.0 | 96.1 | 0.0 | — |
| 34° C./1 µM decitabine | 3 | 5.7 | 11.4 | 93.6 | 65.4 | 5.7 |
| 34° C./1 µM decitabine | 5 | 8.4 | 25.5 | 91.5 | 143.5 | 5.6 |
| 34° C./1 µM decitabine | 7 | 7.6 | 41.5 | 55.0 | 212.5 | 5.1 |
| 34° C./1 µM decitabine | 10 | 2.7 | 56.9 | 21.4 | 206.0 | — |
| 34° C./5 µM decitabine | 0 | 1.8 | 0.0 | 96.1 | 0.0 | — |
| 34° C./5 µM decitabine | 3 | 5.9 | 11.6 | 96.1 | 73.6 | 6.4 |
| 34° C./5 µM decitabine | 5 | 7.2 | 24.7 | 80.3 | 156.5 | 6.3 |
| 34° C./5 µM decitabine | 7 | 6.3 | 38.1 | 62.7 | 218.5 | 5.7 |
| 34° C./5 µM decitabine | 10 | 3.4 | 52.7 | 33.3 | 307.0 | — |
| 34° C./10 µM decitabine | 0 | 1.8 | 0.0 | 96.1 | 0.0 | — |
| 34° C./10 µM decitabine | 3 | 4.7 | 9.8 | 93.6 | 80.8 | 8.3 |
| 34° C./10 µM decitabine | 5 | 4.8 | 19.3 | 75.3 | 151.5 | 7.9 |
| 34° C./10 µM decitabine | 7 | 3.2 | 27.3 | 43.9 | 203.5 | 7.5 |

At 31° C., 10 µM decitabine was the most effective concentration among those tested, yielding an IL-1R-II titer of 378 µg/ml, which is 1.7 times the titer observed at 31° C. with no inducer. Lower IL-1R-II titers are observed at all concentrations of decitabine at 34° C. The highest IL-1R-II titers observed at 34° C. (307 µg/ml) occurred in 5 µM decitabine. Cell viability was reduced at 34° C. as compared to 31° C. Decitabine increased productivity on a per cell basis at 7 and 10 days at all concentrations and temperatures tested.

EXAMPLE 2
Optimization of Temperature and Decitabine Concentration

To determine an optimum temperature and decitabine concentration, three temperatures (30° C., 31° C., and 32° C.) and three decitabine concentrations (10 µM, 15 µM, and 20 µM) were tested. A 31° C. culture containing 0.5 mM sodium butyrate was grown as a control. Butyrate has been shown to induce the production of a variety of specific proteins by cultured mammalian cells. See e.g. International Application Nos. WO 89/06686 and WO 87/05626. The experiment was performed as in Example 1 except that the inducer concentrations, temperatures, and days at which data was collected are as indicated in Table 2 and FIG. 1. Data is shown in Table 2 and FIG. 1.

TABLE 2

| Temperature/Inducer | Day | Viable Cell Density (×10⁶/ml) | Cumulative Viable Cell Density (×10⁶/ml/day) | Viability (%) | IL1R-II Titer (µg/ml) | Productivity (pg IL-1R-II/cell/day) |
|---|---|---|---|---|---|---|
| 30° C./10 µM decitabine | 0 | 2.0 | 0.0 | 94.2 | 0.0 | — |
| 30° C./10 µM decitabine | 3 | 3.0 | 7.4 | 91.8 | 68.2 | 9.2 |
| 30° C./10 µM decitabine | 6 | 1.7 | 14.3 | 70.3 | 156.5 | 10.9 |
| 30° C./10 µM decitabine | 8 | 2.1 | 18.1 | 49.0 | 260.5 | 14.4 |
| 30° C./15 µM decitabine | 0 | 2.0 | 0.0 | 94.2 | 0.0 | — |
| 30° C./15 µM decitabine | 3 | 2.6 | 6.8 | 88.9 | 77.2 | 11.3 |
| 30° C./15 µM decitabine | 6 | 2.2 | 14.0 | 85.9 | 173.0 | 12.4 |
| 30° C./15 µM decitabine | 8 | 1.9 | 18.1 | 33.2 | 283.0 | — |
| 30° C./20 µM decitabine | 0 | 2.0 | 0.0 | 94.2 | 0.0 | — |
| 30° C./20 µM decitabine | 3 | 3.3 | 7.9 | 93.3 | 83.6 | 10.6 |

TABLE 2-continued

| Temperature/Inducer | Day | Viable Cell Density (×10⁶/ml) | Cumulative Viable Cell Density (×10⁶/ml/day) | Viability (%) | IL1R-II Titer (μg/ml) | Productivity (pg IL-1R-II/cell/day) |
|---|---|---|---|---|---|---|
| 30° C./20 μM decitabine | 6 | 2.3 | 16.3 | 77.0 | 219.0 | 13.4 |
| 30° C./20 μM decitabine | 8 | 1.8 | 20.4 | 48.4 | 346.0 | 16.9 |
| 31° C./10 μM decitabine | 0 | 2.0 | 0.0 | 94.2 | 0.0 | — |
| 31° C./10 μM decitabine | 3 | 3.9 | 8.7 | 89.3 | 164.0 | 18.8 |
| 31° C./10 μM decitabine | 6 | 4.3 | 21.0 | 79.6 | 448.5 | 21.3 |
| 31° C./10 μM decitabine | 8 | 3.2 | 28.5 | 63.5 | 1087.0 | 38.1 |
| 31° C./15 μM decitabine | 0 | 2.0 | 0.0 | 94.2 | 0.0 | — |
| 31° C./15 μM decitabine | 3 | 3.3 | 7.9 | 97.6 | 174.0 | 22.0 |
| 31° C./15 μM decitabine | 6 | 4.2 | 19.2 | 78.9 | 440.0 | 22.9 |
| 31° C./15 μM decitabine | 8 | 2.4 | 25.8 | 57.6 | 718.0 | 27.8 |
| 31° C./20 μM decitabine | 0 | 2.0 | 0.0 | 94.2 | 0.0 | — |
| 31° C./20 μM decitabine | 3 | 4.2 | 9.2 | 87.7 | 162.0 | 17.6 |
| 31° C./20 μM decitabine | 6 | 4.2 | 21.7 | 77.9 | 426.0 | 19.6 |
| 31° C./20 μM decitabine | 8 | 2.7 | 28.6 | 57.2 | 774.5 | 27.1 |
| 32° C./10 μM decitabine | 0 | 2.0 | 0.0 | 94.2 | 0.0 | — |
| 32° C./10 μM decitabine | 3 | 3.4 | 8.0 | 85.4 | 186.0 | 23.1 |
| 32° C./10 μM decitabine | 6 | 3.9 | 19.0 | 71.7 | 407.0 | 21.5 |
| 32° C./10 μM decitabine | 8 | 2.1 | 24.9 | 42.3 | 610.5 | 24.5 |
| 32° C./15 μM decitabine | 0 | 2.0 | 0.0 | 94.2 | 0.0 | — |
| 32° C./15 μM decitabine | 3 | 3.4 | 8.0 | 87.6 | 189.0 | 23.5 |
| 32° C./15 μM decitabine | 6 | 3.4 | 18.2 | 65.4 | 410.0 | 22.5 |
| 32° C./15 μM decitabine | 8 | 2.5 | 24.1 | 36.1 | 478.0 | — |
| 32° C./20 μM decitabine | 0 | 2.0 | 0.0 | 94.2 | 0.0 | — |
| 32° C./20 μM decitabine | 3 | 3.6 | 8.3 | 89.1 | 184.5 | 22.2 |
| 32° C./20 μM decitabine | 6 | 3.3 | 18.7 | 64.7 | 492.0 | 26.3 |
| 32° C./20 μM decitabine | 8 | 1.6 | 23.6 | 41.1 | 488.5 | 20.7 |
| 31° C./0.5 mM butyrate | 0 | 2.0 | 0.0 | 94.2 | 0.0 | — |
| 31° C./0.5 mM butyrate | 3 | 4.0 | 8.9 | 91.7 | 214.0 | 23.9 |
| 31° C./0.5 mM butyrate | 6 | 4.0 | 20.9 | 88.5 | 473.0 | 22.6 |
| 31° C./0.5 mM butyrate | 8 | 3.9 | 28.9 | 71.1 | 862.0 | 29.8 |

Figure 1:
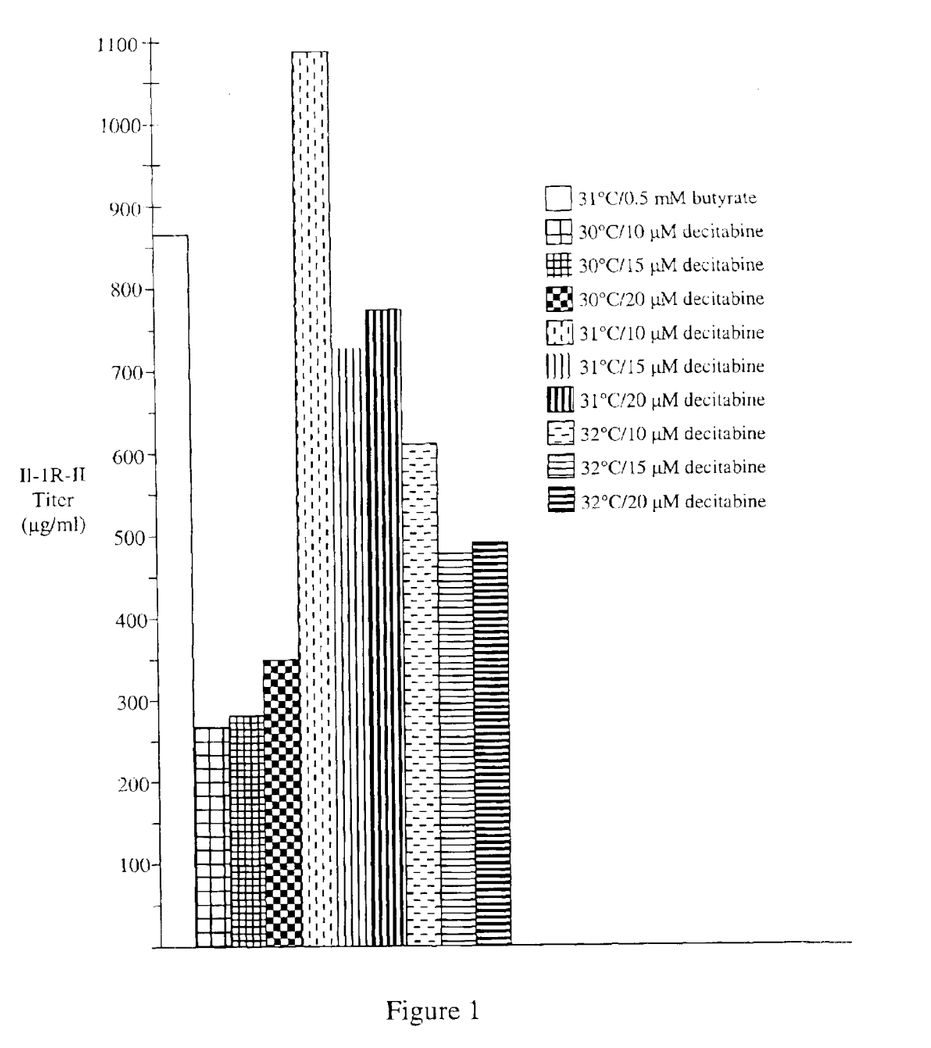
FIG. 1 shows the interleukin-1 receptor type II (IL-1-R-II) titer in the medium after 8 days of culture under the indicated culture conditions.

FIG. 1 shows that incubation at 31° C. enabled 25H9 cells to produce more IL-1R-II in the presence of 10 μM decitabine than incubation at either 30° C. or 32° C. The highest titers of IL-1R-II (1087 μg/ml) were observed in a culture incubated for 8 days at 31° C. in medium containing 10 μM decitabine, which had a higher titer than a culture containing 0.5 mM sodium butyrate grown at 31° C. for 8 days. Cells cultured in 10 μM decitabine also produced more IL-1R-II at 32° C. than did cells cultured in 15 μM or 20 μM decitabine. However, among the cells cultured at 30° C., the cells cultured in 20 FM decitabine produced a higher titer of IL-1R-II than cells cultured in either 10 μM or 15 μM decitabine. Productivity on a per cell basis of all cultures grown in decitabine at 31° C. was comparable to, and in some cases greater than, the productivity of the control culture grown in butyrate at 31° C. Higher titers observed in this example as compared to Example 1 are due to variability in the reagents used in the ELISA assay.

EXAMPLE 3

Induction with 5-Bromo-2'-Deoxycytidine 5'-Monophosphate

The following experiment compares the effects of 5-bromo-2'-deoxycytidine 5'-monophosphate and 5-aza-2'-deoxycytidine on induction of protein production. The experiment was done as described in Example 1 with the following exceptions. The inducers, concentrations, and days at which samples were taken were as indicated in Table 3. All cultures were incubated at 31° C., and cell number and viability were determined using a Guava PCA Cytometer (available from Guava Technologies, Hayward, Calif., USA). Samples were done in triplicate. Data is shown in Table 3.

TABLE 3

| | | Induction with 5-bromo-2'-deoxycytidine 5'-monophosphate | | | |
|---|---|---|---|---|---|
| Inducing agent and its concentration (μM) | Day | Viable cell density (cells/ml × 10⁶) | Cumulative viable cell density (cells mL/day) | Productivity (pg of IL-1RII/cell/day) | Titer of IL-1R-II (mg/L) |
| 5-aza-2'-deoxycytidine (10 μM) | 0 | 2.4 | 0 | — | 0.0 |
| 5-aza-2'-deoxycytidine (10 μM) | 2 | 2.4 | 4.8 | 12.2 | 58.5 |
| 5-aza-2'-deoxycytidine (10 μM) | 5 | 1.8 | 11.1 | 13.3 | 148.5 |
| 5-aza-2'-deoxycytidine (10 μM) | 7 | 1.1 | 14.0 | 14.1 | 197.5 |
| 5-aza-2'-deoxycytidine (10 μM) | 9 | 0.9 | 16.0 | 14.9 | 238.4 |

TABLE 3-continued

Induction with 5-bromo-2'-deoxycytidine 5'-monophosphate

| Inducing agent and its concentration (μM) | Day | Viable cell density (cells/ml × 10⁶) | Cumulative viable cell density (cells mL/day) | Productivity (pg of IL-1RII/ cell/day) | Titer of IL-1R-II (mg/L) |
|---|---|---|---|---|---|
| 5-bromo-2'-deoxycytidine 5' monophosphate (5 μM) | 0 | 2.4 | 0.0 | — | 0.0 |
| 5-bromo-2'-deoxycytidine 5' monophosphate (5 μM) | 2 | 3.1 | 5.5 | 12.4 | 67.6 |
| 5-bromo-2'-deoxycytidine 5' monophosphate (5 μM) | 5 | 2.8 | 14.3 | 13.8 | 197.4 |
| 5-bromo-2'-deoxycytidine 5' monophosphate (5 μM) | 7 | 2.3 | 19.4 | 14.9 | 289.1 |
| 5-bromo-2'-deoxycytidine 5' monophosphate (5 μM) | 9 | 1.8 | 23.5 | 15.2 | 357.6 |
| 5-bromo-2'-deoxycytidine 5' monophosphate (10 μM) | 0 | 2.4 | 0.0 | — | 0.0 |
| 5-bromo-2'-deoxycytidine 5' monophosphate (10 μM) | 2 | 3.3 | 5.6 | 13.4 | 75.0 |
| 5-bromo-2'-deoxycytidine 5' monophosphate (10 μM) | 5 | 3.0 | 15.0 | 17.6 | 264.0 |
| 5-bromo-2'-deoxycytidine 5' monophosphate (10 μM) | 7 | 2.8 | 20.9 | 19.2 | 401.4 |
| 5-bromo-2'-deoxycytidine 5' monophosphate (10 μM) | 9 | 2.3 | 26.0 | 18.6 | 484.0 |
| 5-bromo-2'-deoxycytidine 5' monophosphate (15 μM) | 0 | 2.4 | 0.0 | — | 0.0 |
| 5-bromo-2'-deoxycytidine 5' monophosphate (15 μM) | 2 | 3.0 | 5.4 | 11.4 | 61.4 |
| 5-bromo-2'-deoxycytidine 5' monophosphate (15 μM) | 5 | 2.6 | 13.8 | 12.1 | 167.3 |
| 5-bromo-2'-deoxycytidine 5' monophosphate (15 μM) | 7 | 2.2 | 18.6 | 13.4 | 249.1 |
| 5-bromo-2'-deoxycytidine 5' monophosphate (15 μM) | 9 | 1.6 | 22.4 | 14.2 | 318.3 |

These data indicate that 5-bromo-2'-deoxycytidine 5'-monophosphate can be about twice as effective as 5-aza-2'-deoxycytidine at inducing of protein production. A concentration of 10 μM 5-bromo-2'-deoxycytidine 5' monophosphate was more effective than either 5 μM or 15 μM at inducing IL-1R-II production, although all three concentrations tested were more effective than 10 μM 5-aza-2'-deoxycytidine. Moreover, viable cell density was higher at all three 5-bromo-2'-deoxycytidine 5' monophosphate concentrations tested that it was at 10 μM 5-aza-2'-deoxycytidine.

What is claimed is:

1. A method for producing a protein comprising culturing Chinese hamster ovary (CHO) cells that produce the protein in the presence of a cytidine analogue in the culture medium, wherein the presence of the cytidine analogue in the culture medium results in an increase in the production of the protein and wherein the culture medium is serum free.

2. The method of claim 1, wherein the CHO cells are cultured at a temperature from about 29° C. to 36° C.

3. The method of claim 1, wherein the cytidine analogue is 5-aza-2'-deoxycytidine with or without one or more phosphate group(s) attached to the 3' and/or 5' carbon(s).

4. The method of claim 3, wherein the concentration of 5-aza-2'-deoxycytidine with or without one or more phosphate group(s) attached to the 3' and/or 5' carbon(s) is from about 0.1 μM to about 50 μM.

5. The method of claim 1, wherein the cytidine analogue is 5-bromo-2'-deoxycytidine with or without one or more phosphate group(s) attached to the 3' and/or 5' carbon(s).

6. The method of claim 5, wherein the concentration of 5-bromo-2'-deoxycytidine with or without one or more phosphate group(s) attached to the 3' and/or 5' carbon(s) is from about 0.1 μM to about 50 μM.

7. The method of claim 1, wherein the cytidine analogue in the medium is at a concentration from about 0.01 μM to about 100 μM.

8. The method of claim 1, wherein the protein is an antibody.

9. The method of claim 1, wherein the protein is a recombinant protein.

10. The method of claim 1, wherein the messenger RNA encoding the protein is transcribed starting from a viral promoter.

11. The method of claim 1, wherein the volume of the cell culture is at least about 100 liters.

12. The method of claim 1, wherein the protein is secreted into, the medium.

13. A method for producing a recombinant protein comprising culturing mammalian cells in a medium comprising a DNA demethylating agent at a temperature from about 29° C. to 36° C., wherein the recombinant protein is secreted into the medium by the mammalian cells, and harvesting the medium comprising the recombinant protein, wherein the mammalian cells have been genetically engineered to produce the recombinant protein, and wherein the presence of the DNA demethylating agent in the medium results in an increase in the amount of the recombinant protein in the medium.

14. The method of claim 13, wherein the DNA demethylating agent is a cytidine analogue.

15. The method of claim 14, wherein the cytidine analogue is 5-aza-2'-deoxycytidine with or without one or more phosphate group(s) attached to the 3' and/or 5' carbon(s).

16. The method of claim 15, wherein the concentration of 5-aza-2'-deoxycytidine with or without one or more phosphate group(s) attached to the 3' and/or 5' carbon(s) is from about 0.1 $\mu$M to about 50 $\mu$M.

17. The method of claim 14, wherein the cytidine analogue is at a concentration from about 0.01 $\mu$M to about 100 $\mu$M.

18. The method of claim 14, wherein the cytidine analogue is 5-bromo-2'-deoxycytidine with or without one or more phosphate group(s) attached to the 3' and/or 5' carbon (s) at a concentration from about 0.1 $\mu$M to about 50 $\mu$M.

19. The method of claim 13, wherein the medium is serum free.

20. The method of claim 13, wherein the mammalian cells are CHO cells.

21. The method of claim 13, wherein the recombinant protein is an antibody.

22. A method for producing a recombinant protein comprising
culturing CHO cells in a medium comprising 5-aza-2'-deoxycytidine at a concentration from about 1.0 $\mu$M to about 20 $\mu$M at a temperature of less than 37° C., wherein the CHO cells secrete the recombinant protein into the medium and wherein the medium is serum free, and
collecting the medium comprising the recombinant protein.

23. A method for producing a recombinant protein comprising
culturing CHO cells in a medium comprising 5-bromo-2'-deoxycytidine 5'-monophosphate at a concentration from about 1.0 $\mu$M to about 20 $\mu$M at a temperature of less than 37° C., wherein the CHO cells secrete the recombinant protein into the medium and wherein the medium is serum free, and
collecting the medium comprising the recombinant protein.

24. A CHO cell culture comprising:
a medium comprising 5-aza-2'-deoxycytidine with or without one or more phosphate group(s) attached to the 3' and/or 5' carbon(s) at a concentration from about 0.1 $\mu$M to about 50 $\mu$M, wherein the medium is serum free; and
a CHO cell line that has been genetically engineered to express a recombinant, secreted protein.

25. A mammalian cell culture comprising:
a medium comprising 5-aza-2'-deoxycytidine with or without one or more phosphate group(s) attached to the 3' and/or 5' carbon(s) at a concentration from about 0.1 $\mu$M to about 50 $\mu$M, wherein the medium is serum free; and
a mammalian cell line that can express an antibody.

26. A CHO cell culture comprising:
a medium comprising 5-bromo-2'-deoxycytidine with or without one or more phosphate group(s) attached to the 3' and/or 5' carbon(s) at a concentration from about 0.1 $\mu$M to about 50 $\mu$M, wherein the medium is serum free; and
a CHO cell line that has been genetically engineered to express a recombinant, secreted protein.

27. A mammalian cell culture comprising:
a medium comprising 5-bromo-2'-deoxycytidine with or without one or more phosphate group(s) attached to the 3' and/or 5' carbon(s) at a concentration from about 0.1 $\mu$M to about 50 $\mu$M, wherein the medium is serum free; and
a mammalian cell line that can express an antibody.

28. A method for producing a protein comprising culturing CHO cells that produce the protein in the presence of 5-aza-2'-deoxycytidine with or without one or more phosphate group(s) attached to the 3' and/or 5' carbon(s) at a temperature from about 29° C. to 36° C., wherein the presence of the 5-aza-2'-deoxycytidine results in an increase in the production of the protein.

29. A method for producing a protein comprising culturing CHO cells that produce the protein in the presence of 5-bromo-2'-deoxycytidine with or without one or more phosphate group(s) attached to the 3' and/or 5' carbon(s), wherein the presence of the 5-bromo-2'-deoxycytidine results in an increase in the production of the protein.

* * * * *